US010562924B2

(12) United States Patent
Endo et al.

(10) Patent No.: US 10,562,924 B2
(45) Date of Patent: *Feb. 18, 2020

(54) PHOSPHORUS-CONTAINING COMPOUND, AND CURABLE EPOXY RESIN COMPOSITION CONTAINING SAME

(71) Applicant: ADEKA CORPORATION, Tokyo (JP)

(72) Inventors: Takeshi Endo, Fukuoka (JP); Kozo Matsumoto, Fukuoka (JP); Ken-ichi Tamaso, Saitama (JP); Ryo Ogawa, Saitama (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/900,844

(22) PCT Filed: Aug. 21, 2014

(86) PCT No.: PCT/JP2014/071825
§ 371 (c)(1),
(2) Date: Dec. 22, 2015

(87) PCT Pub. No.: WO2015/025904
PCT Pub. Date: Feb. 26, 2015

(65) Prior Publication Data
US 2016/0152643 A1 Jun. 2, 2016

(30) Foreign Application Priority Data

Aug. 22, 2013 (JP) .................................. 2013-171940

(51) Int. Cl.
| C07F 9/36 | (2006.01) |
| C07F 9/32 | (2006.01) |
| C09K 21/12 | (2006.01) |
| C09K 21/14 | (2006.01) |
| C08L 63/00 | (2006.01) |
| C08K 5/5313 | (2006.01) |

(52) U.S. Cl.
CPC .......... *C07F 9/3282* (2013.01); *C07F 9/3264* (2013.01); *C07F 9/36* (2013.01); *C08K 5/5313* (2013.01); *C08L 63/00* (2013.01); *C09K 21/12* (2013.01); *C09K 21/14* (2013.01)

(58) Field of Classification Search
CPC ... C07F 9/32; C07F 9/36; C09K 21/12; C09K 21/14; C08L 63/00
See application file for complete search history.

(56) References Cited

U.S. PATENT DOCUMENTS

| 3,151,146 A | 9/1964 | Schrader et al. |
| 3,371,046 A | 2/1968 | McCord |
| 3,527,850 A | 9/1970 | McHugh et al. |
| 4,111,900 A | 9/1978 | Noetzel et al. |
| 5,739,187 A | 4/1998 | Asano et al. |

| 6,339,168 B1 | 1/2002 | Klatt et al. |
| 2011/0245386 A1 | 10/2011 | Hill et al. |
| 2012/0153424 A1 | 6/2012 | Oh et al. |

FOREIGN PATENT DOCUMENTS

| DE | 1956187 | 5/1971 |
| DE | 251 134 | 11/1987 |
| EP | 1044981 A1 | 10/2000 |
| GB | 991590 | 5/1965 |
| GB | 1121462 | 7/1968 |
| JP | S52-39630 | 3/1977 |
| JP | 10-195178 | 7/1998 |
| JP | 10-265487 | 10/1998 |
| JP | 2002-526585 | 8/2002 |
| JP | 2012-512196 | 5/2012 |
| KR | 2009-0073474 | 7/2009 |
| KR | 2009-0122819 | 12/2009 |
| SU | 584008 | 12/1977 |
| WO | 00/17268 | 3/2000 |
| WO | WO 2009/119789 | 10/2009 |
| WO | WO 2014/206487 | 12/2014 |

OTHER PUBLICATIONS

Ginjaar et al., caplus an 1966:490172, 1966.*
Kamai et al., caplus an 1957:62173, 1957.*
Schindlbauer, 1966, caplus an 1966:67931.*
Osborne et al., 1965, caplus an 1965:427345.*
Nasirov et al., 1985, caplus an 1985:406448.*
Kim et al., 2012, caplus an 2012:962181.*
Lee et al., 2009, caplus an 2009:828744, caplus abstract of KR 2009073474.*
International Search Report, PCT/JP2014/071825, dated Nov. 25, 2014.
Jon J. Longlet et al., Synthesis, Structure, and Reactivity of Some N- Phosphorylphosphoranimines, Inorganic Chemistry, 2002, vol. 41, No. 24, 6507-6513.
Written Opinion, PCT/JP2014/071825, dated Nov. 25, 2014.
Supplementary European Search Report dated Mar. 31, 2017 in corresponding European Patent Application No. 14837177.6
Drabowicz, J. et al., "Product class 14: dialkylphosphinic acids and derivatives", Database CA [Online], Chemical Abstracts Service, Columbus, OH, US, 2009, retrieved from STN, Database accession No. 2009-453330, XP-002768307.
Platel et al., "A Series of Bis(phosphinic)diamido Yttrium Complexes As Initiators for Lactide Polymerization," Inorganic Chemistry, vol. 47, No. 15, 2008, pp. 6840-6849.
Jacob et al., "Mass Spectrometry of Dimethylthiophosphinates of Aromatic Hydroxy Compounds," Biomedical Mass Spectrometry, vol. 5, No. 4, 1978, pp. 302-311.

(Continued)

*Primary Examiner* — Sun Jae Yoo
(74) *Attorney, Agent, or Firm* — Young & Thompson

(57) ABSTRACT

The purpose of the present invention is to provide a phosphorus-containing compound having reactivity with a glycidyl group, specifically a phosphorus-containing compound represented by general formula (I). (In the formula, m represents a numerical value of 1 to 10; $R_1$ and $R_2$ independently represent a hydrogen atom, an alkyl group or an aryl group; $R_3$ represents an alkyl group, an alkanediyl group, an alkanetriyl group, an alkanetetrayl group or an aromatic group; X represents an oxygen atom or a sulfur atom; Y represents an oxygen atom, a sulfur atom or —$NR_4$—; and $R_4$ represents a hydrogen atom, an alkyl group or an aryl group.)

4 Claims, 6 Drawing Sheets

(56) References Cited

OTHER PUBLICATIONS

Kim et al., Chelating Bis(thiophosphinic amidate)s as Versatile Supporting Ligands for the Group 3 Metals. An Application to the Synthesis of Highly Active Catalysts for Intramolecular Alkene Hydroamination, J. Am. Chem. Soc., 2003, 125, pp. 9580-9561.

Dhawan et al., "Lithiation-Induced 1,3-Migrations of P(IV) Groups from Heteroatom to the Naphthalene Ring," J. Org. Che. 1991, 56, 833-835.

Hagaman, "Local Structure Evaluation in Solid Organophosphorus Compounds by Double Cross Polarization Carbon-13 Nuclear Magnetic Resonance Spectroscopy," J. Am. Chem. Soc. 1998, 110, 5594-5595.

Kayan et al., "Synthesis and reactivity of bis(diphenylphosphino)amine ligands and their application in Suzuki cross-coupling reactions," Inorganica Chimica Acta 385 (2012) 164-169.

* cited by examiner

[Fig. 1]
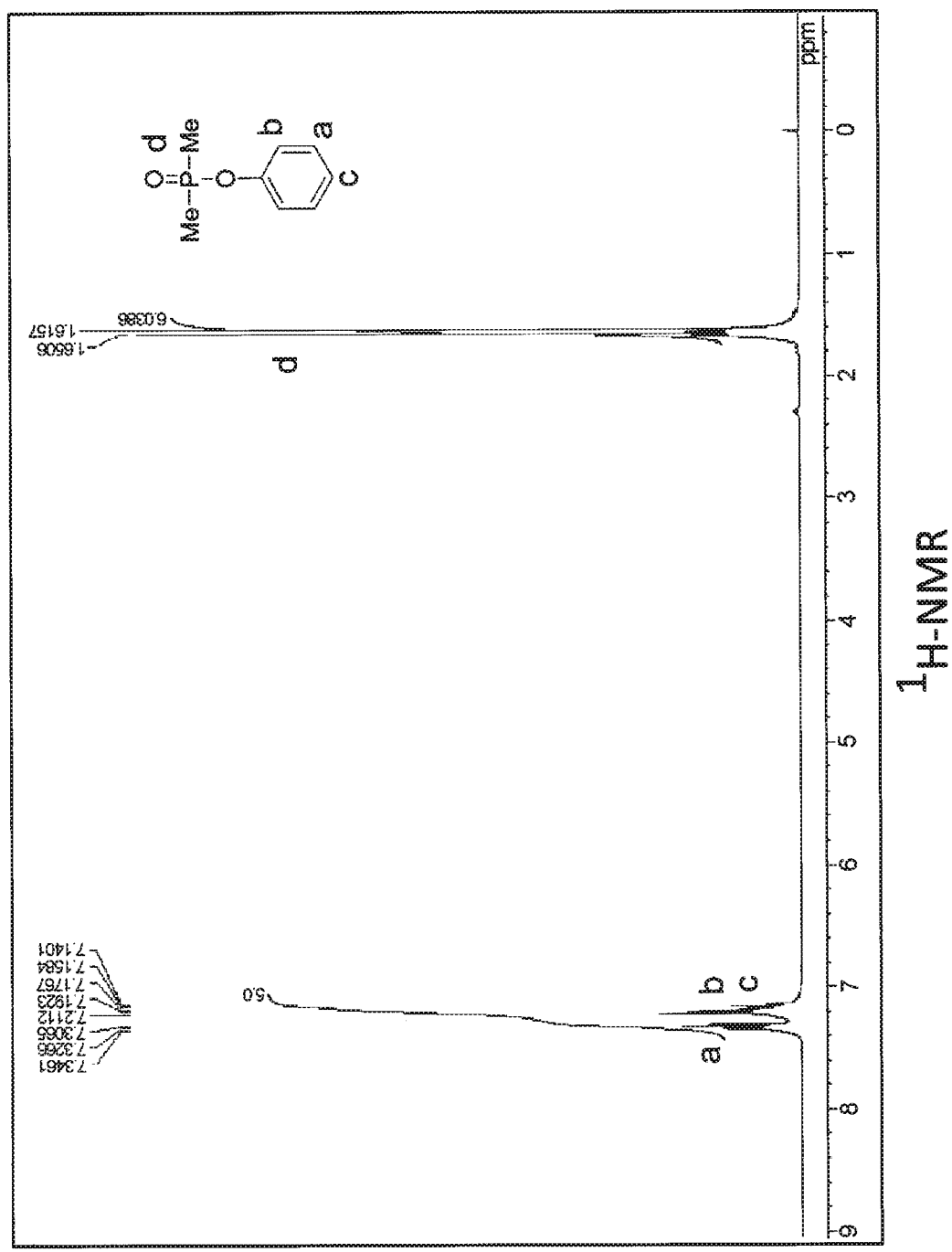

[Fig. 2]
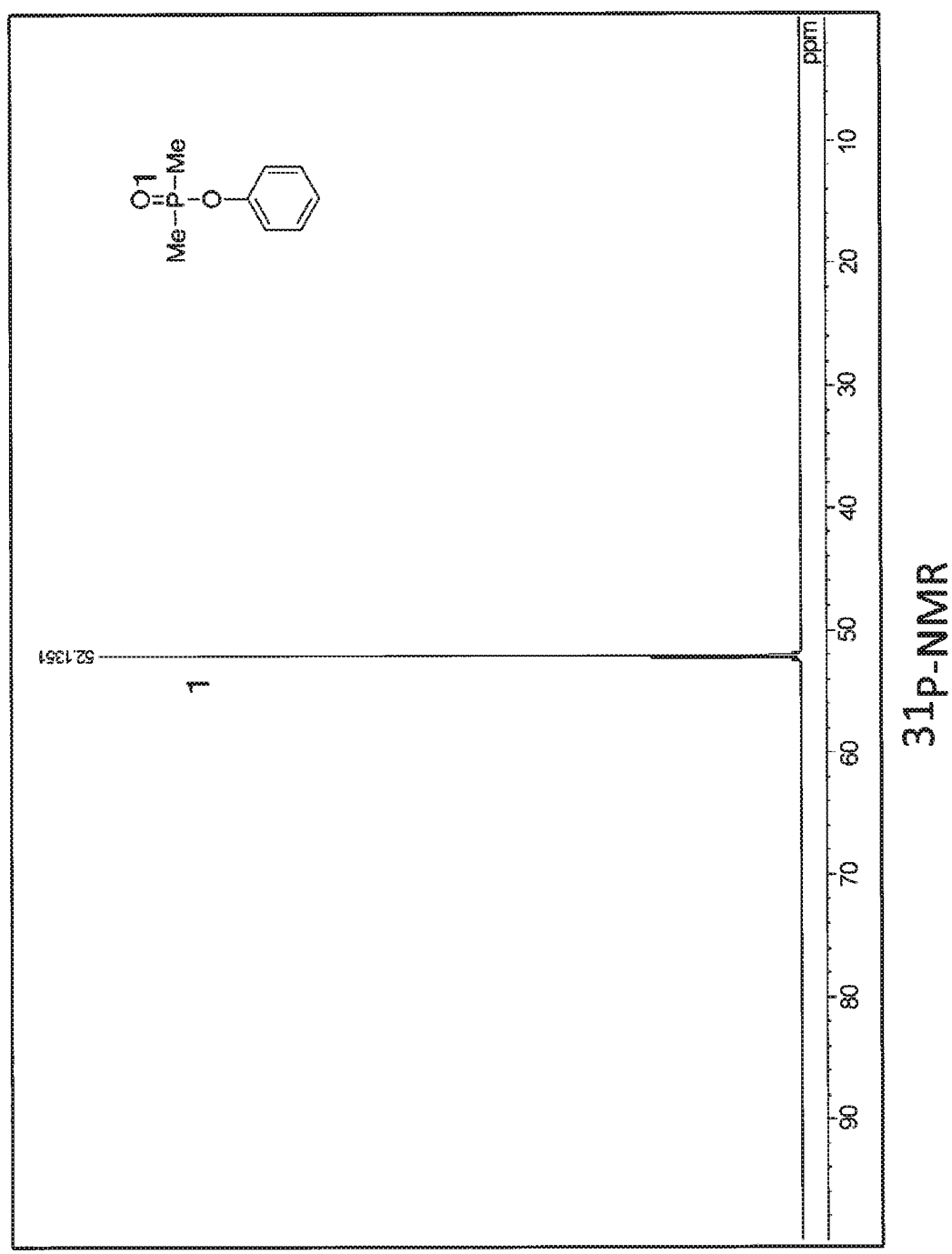

[Fig. 3]
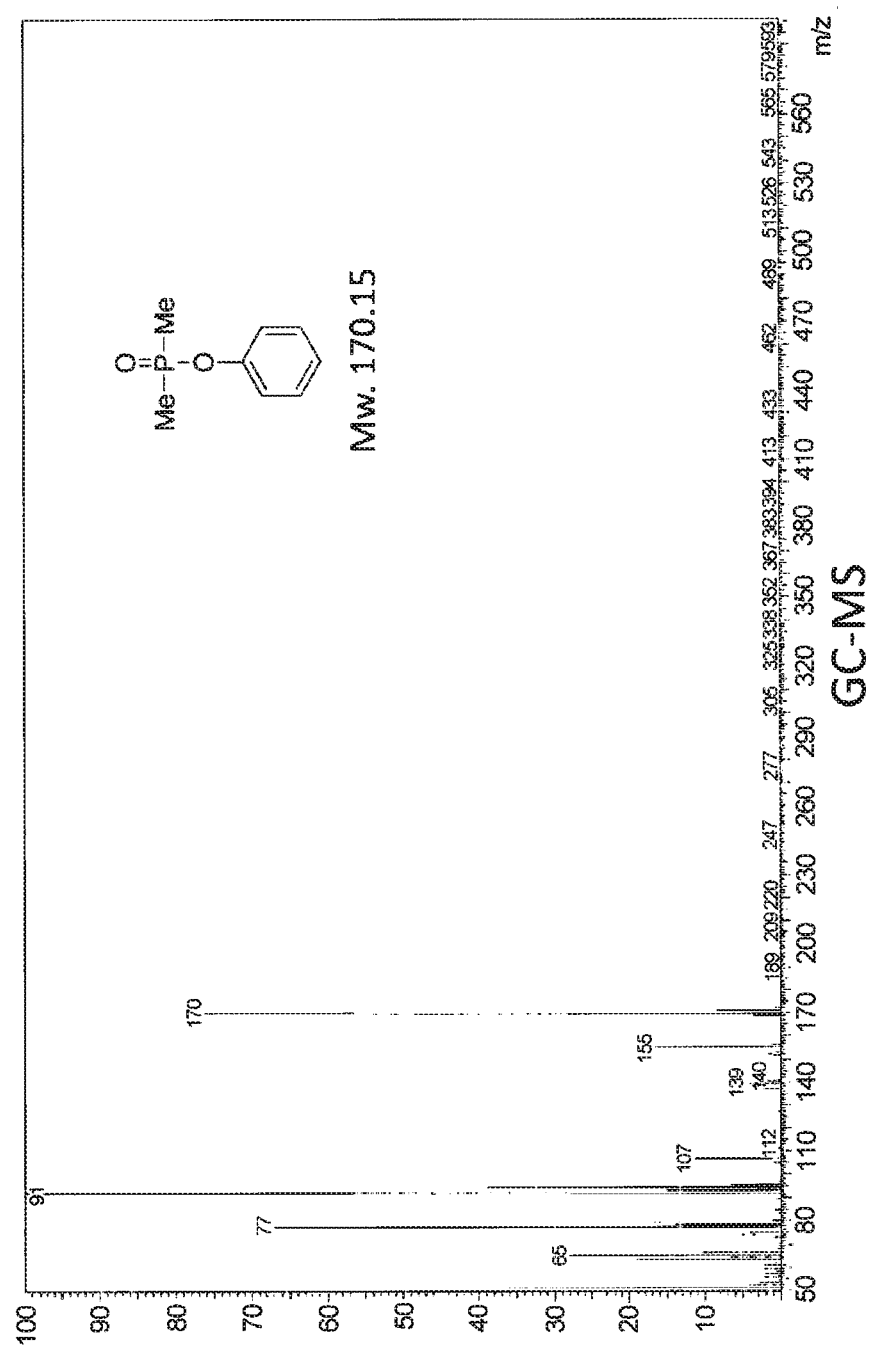

[Fig. 4]
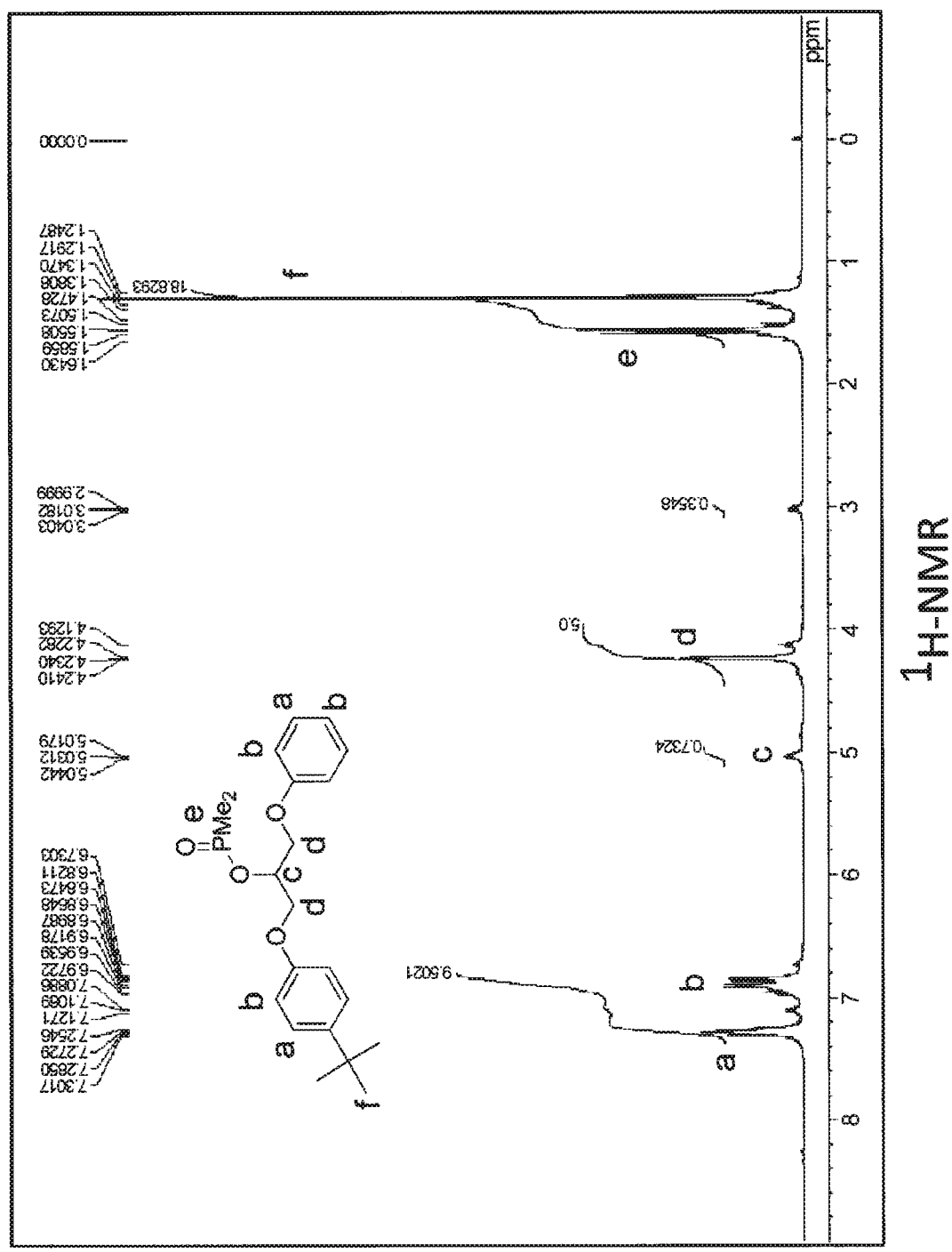

[Fig. 5]
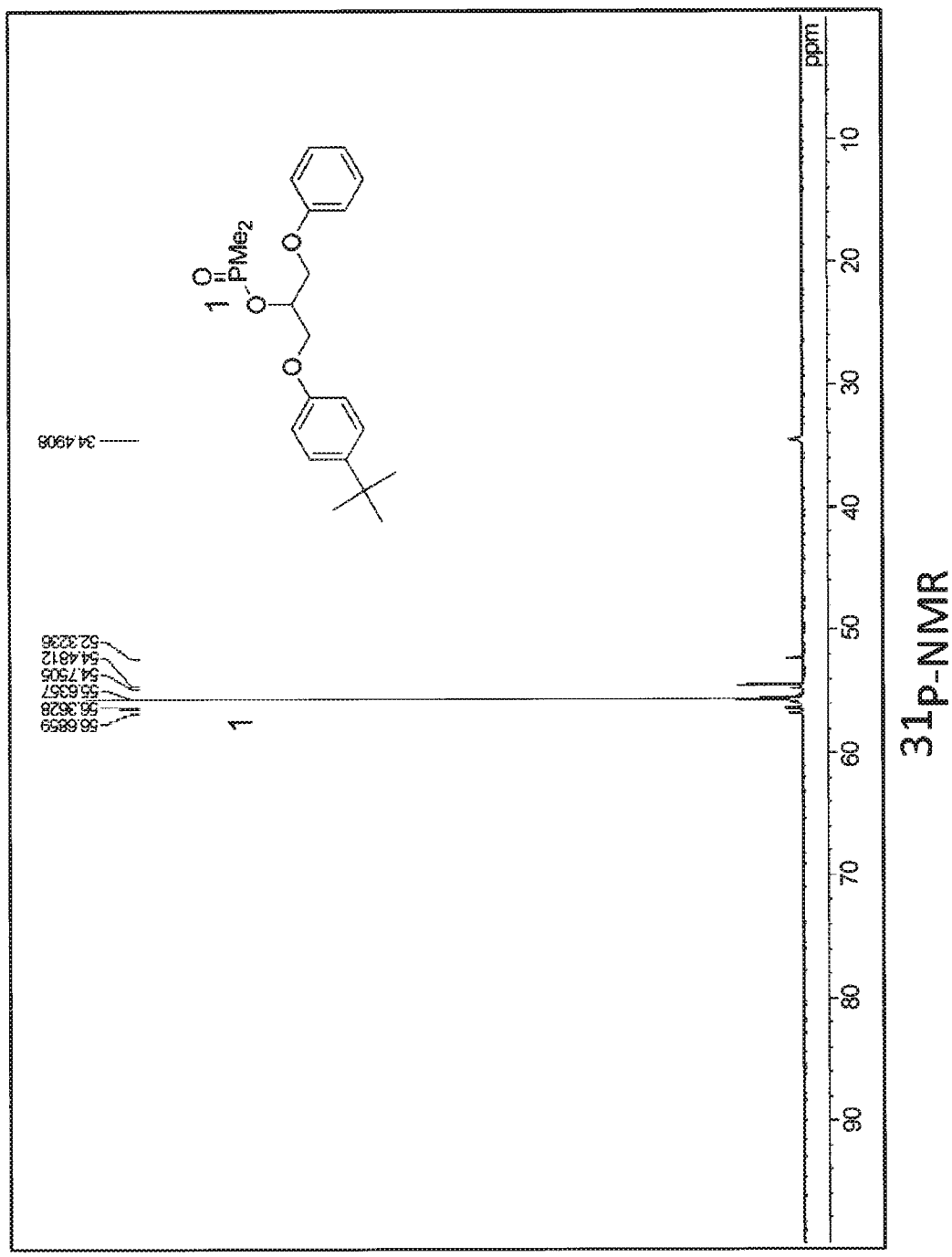

[Fig. 6]
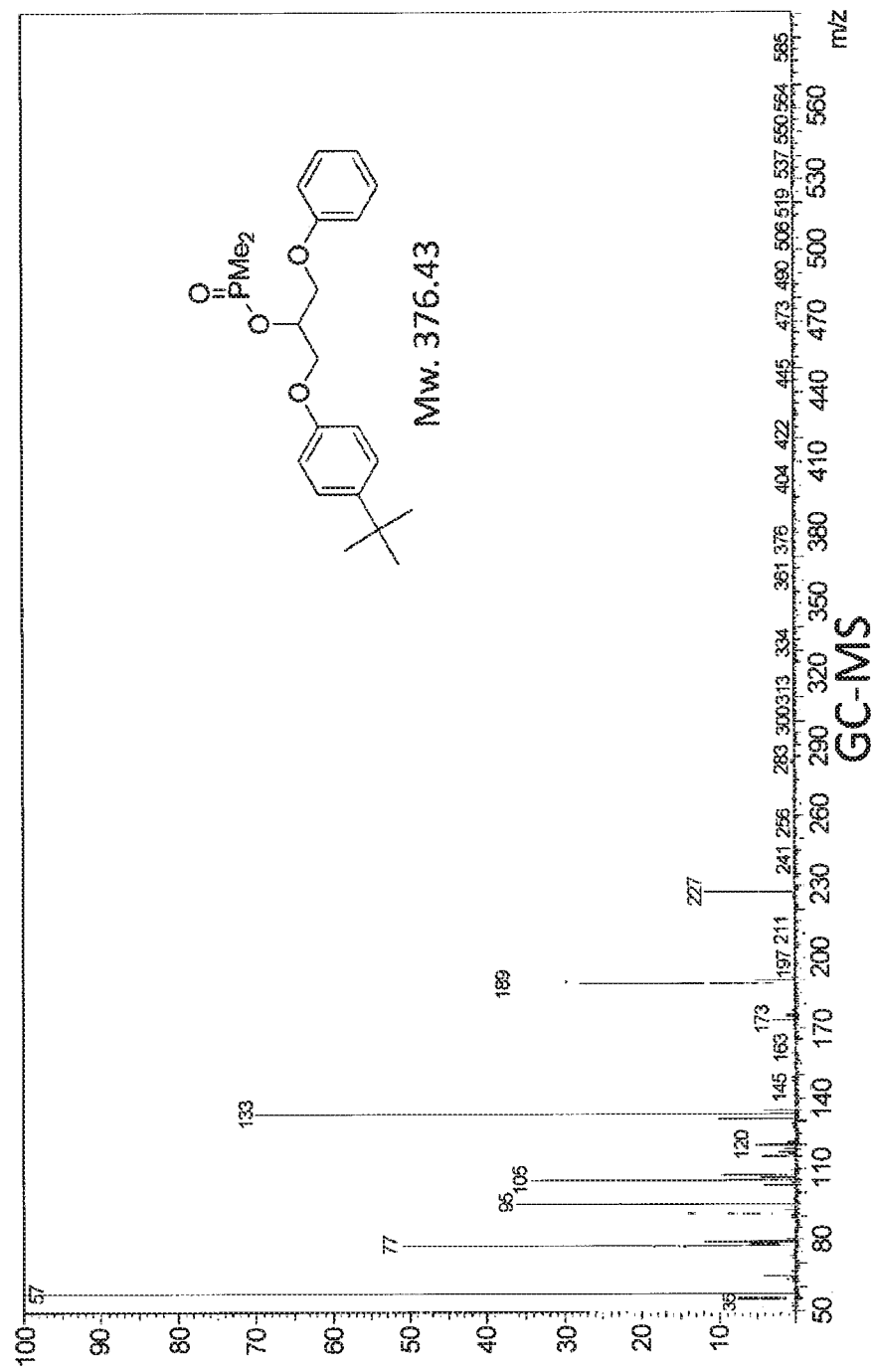

PHOSPHORUS-CONTAINING COMPOUND, AND CURABLE EPOXY RESIN COMPOSITION CONTAINING SAME

TECHNICAL FIELD

This invention relates to a phosphorus-containing compound, particularly a reactive phosphorus-containing compound that can be combined with a polyepoxy compound to provide a curing epoxy resin composition expected to provide flame retardation, reduced dielectric constant, and the like.

BACKGROUND ART

The recent increase in concern with global environmental problem and safety of the human body has boosted the demand for less hazard and more safety, as well as flame retardancy, of electric/electronic products. That is, reduction of harmful gas and smoke generation has been demanded.

Use of a bromine-containing flame retardant, which provides good flame retardancy, has been being limited on account of generation of toxic hydrogen halide gas (hydrogen bromide) on combustion. Therefore, studies have been directed to compositions containing an ordinary epoxy resin and a halogen-free flame retardant, such as a nitrogen compound, a phosphorus compound, or an inorganic compound. However, these additives for imparting flame retardancy are disadvantageous in that their flame retardant effect is insufficient or they adversely affect curing of the epoxy resin or are accompanied by reduction of physical properties, such as a glass transition temperature, of a cured product.

For example, triphenyl phosphate is widely used as a phosphorous-containing flame retardant for various resins. Patent Literature 1 described below proposes adding a phosphorus-containing flame retardant composed of a high-molecular-weight divalent phenol and a phenol to an epoxy resin. Nevertheless, the proposed flame retardant should be used in a large quantity in order to impart sufficient flame retardancy to an epoxy resin. Adding a sufficient amount of the flame retardant to realize satisfactory flame retardation causes reduction in glass transition temperature, whereas an increase in glass transition temperature results in insufficient flame retardancy. Patent Literature 2 below proposes using a reactive phosphoric ester compound. The proposal has turned out to be impractical because incorporating the phosphoric ester compound into an epoxy resin makes the resin hygroscopic or makes part of the resin take on a three-dimensional structure, which increases the viscosity and thereby greatly reduces the workability of the resin composition.

CITATION LIST

Patent Literature

Patent Literature 1: U.S. Pat. No. 5,739,187(A)
Patent Literature 2: JP 10-195178A

SUMMARY OF INVENTION

Technical Problem

An object of the invention is to provide a phosphorus-containing compound having reactivity with a glycidyl group, particularly a phosphorus-containing compound capable of providing a curing epoxy resin composition with flame retardancy and a low dielectric constant.

Solution to Problem

As a result of extensive investigations, the inventors have found that a specific phosphorus-containing compound accomplishes the above object and reached the present invention.

The present invention provides a phosphorus-containing compound represented by following general formula (I).

[Chem. 1]

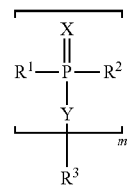

(I)

wherein m represents a number of 1 to 10; $R^1$ and $R^2$ each independently represent a hydrogen atom, an alkyl group, or an aryl group; $R^3$ represents an alkyl group, an alkanediyl group, an alkanetriyl group, an alkanetetrayl group, or an aromatic group; X represents an oxygen atom or a sulfur atom; Y represents an oxygen atom, a sulfur atom, or —$NR^4$—; and $R^4$ represents a hydrogen atom, an alkyl group, or an aryl group.

Advantageous Effects of Invention

The invention provides a phosphorus-containing compound having excellent reactivity with an epoxy resin and promising to impart flame retardation to the epoxy resin and to reduce the dielectric constant of the epoxy resin.

BRIEF DESCRIPTION OF DRAWINGS

FIG. 1 is a $^1$H-NMR spectrum of the phosphorus-containing compound obtained in Example 1.
FIG. 2 is a $^{31}$P-NMR spectrum of the phosphorus-containing compound obtained in Example 1.
FIG. 3 is a GC-MS spectrum of the phosphorus-containing compound obtained in Example 1.
FIG. 4 is a $^1$H-NMR spectrum of P2 obtained in Example 2.
FIG. 5 is a $^{31}$P-NMR spectrum of P2 obtained in Example 2.
FIG. 6 is a GC-MS spectrum of P2 obtained in Example 2.

DESCRIPTION OF EMBODIMENTS

The phosphorus-containing compound according to the invention will be described in detail.

Examples of the alkyl group as represented by $R^1$ and $R^2$ in general formula (I) include methyl, ethyl, propyl, isopropyl, butyl, isobutyl, tert-butyl, amyl, isoamyl, tert-amyl, hexyl, isohexyl, octyl, 2-ethylhexyl, tert-octyl, nonyl, and decyl. Examples of the aryl group as represented by $R^1$ and $R^2$ are phenyl and naphthyl. Examples of the alkyl group as represented by $R^3$ include methyl, ethyl, propyl, isopropyl, butyl, isobutyl, tert-butyl, amyl, isoamyl, tert-amyl, hexyl, isohexyl, octyl, 2-ethylhexyl, tert-octyl, nonyl, and decyl. Examples of the aryl group as represented by $R^3$ include phenyl and naphthyl. Examples of the alkanediyl group as $R^3$ include methylene, ethylene, propylene, butylene, and octylene. Examples of the alkanetriyl group as $R^3$ are methylenetriyl and 1,1,3-ethylenetriyl. The alkanetetrayl as $R^3$ is exemplified by 1,1,2,2-ethylenetriyl. Examples of the aromatic group as represented by $R^3$ include those derived from mononuclear polyhydric phenol compounds, such as hydroquinone, resorcin, pyrocatechol, and phloroglucinol, and polynuclear polyhydric phenol compounds, such as dihydroxynaphthalene, biphenol, methylenebisphenol (bisphenol F), methylenebis(o-cresol), ethylidenebisphenol, isopropylidenebisphenol (bisphenol A), isopropylidenebis(o-cresol), tetrabromobisphenol A, 1,3-bis(4-hydroxycumylbenzene), 1,4-bis(4-hydroxycumylbenzene), 1,1,3-tris(4-hydroxyphenyl)butane, 1,1,2,2-tetra(4-hydroxyphenyl)ethane, thiobisphenol, sulfonylbisphenol, oxybisphenol, phenol novolak, o-cresol novolak, ethylphenol novolak, butylphenol novolak, octylphenol novolak, resorcin novolak, and terpene phenol. Preferred of them are groups represented by the formulae shown below.

[Chem. 2]

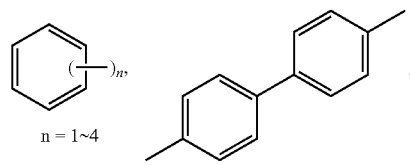

n = 1~4

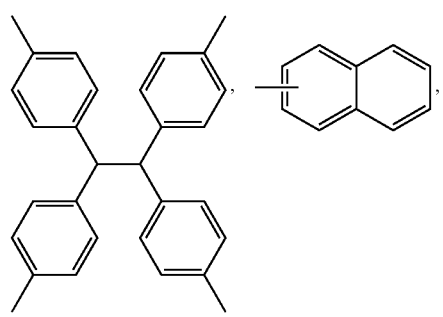

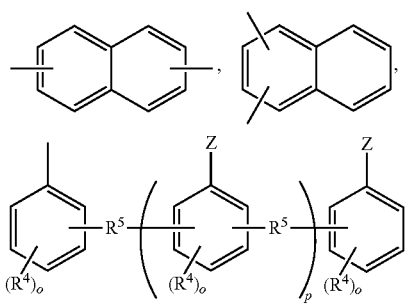

$R^4$ = H, C1 to C4 Alkyl group o = 1~3  p = 0~50

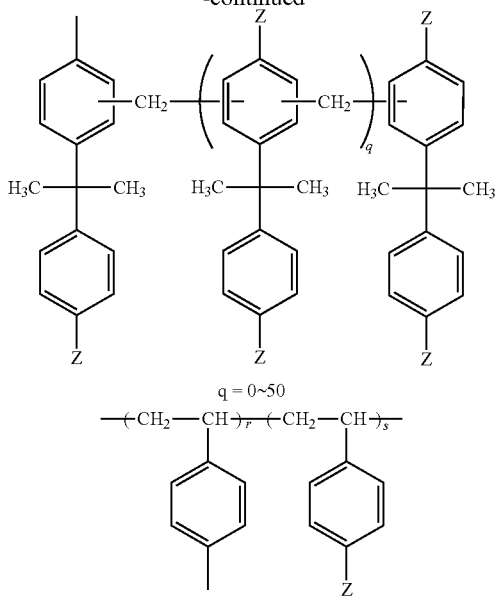

q = 0~50

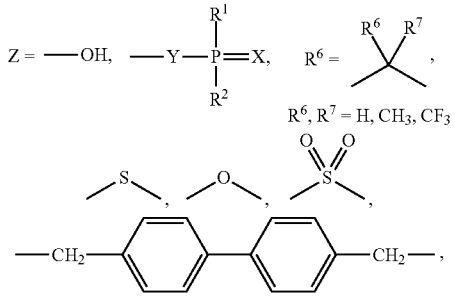

r = 0~25
s = 0~25

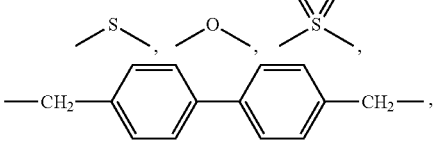

$R^6$, $R^7$ = H, $CH_3$, $CF_3$

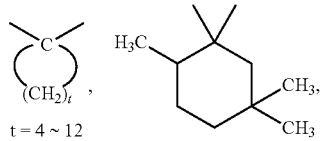

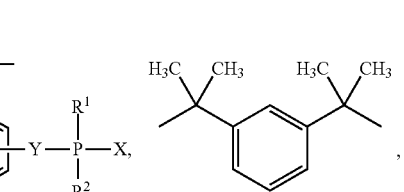

t = 4~12

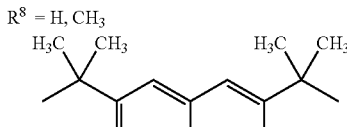

$R^8$ = H, $CH_3$

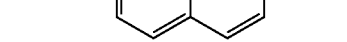

The phosphorus-containing compounds of the invention are preferably those of general formula (I) in which $R^1$ is C1-C5 alkyl, $R^2$ is C1-C5 alkyl, $R^3$ is an aromatic group; and X and Y are each oxygen.

Specific examples of the phosphorus-containing compound of the invention include those represented by formulae (I-1) through (I-8) described below.

[Chem. 3]

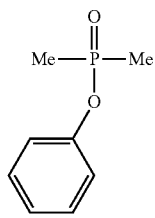
(I-1)

[Chem. 4]

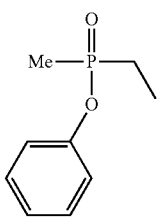
(I-2)

[Chem. 5]

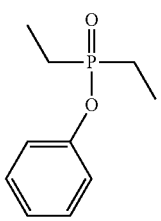
(I-3)

[Chem. 6]

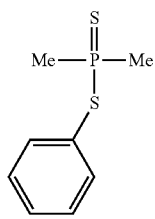
(I-4)

[Chem. 7]

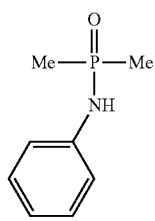
(I-5)

[Chem. 8]

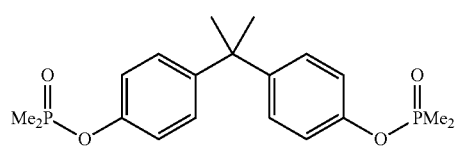
(I-6)

[Chem. 9]

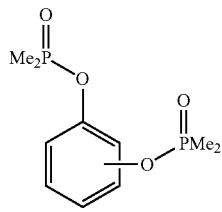
(I-7)

[Chem. 10]

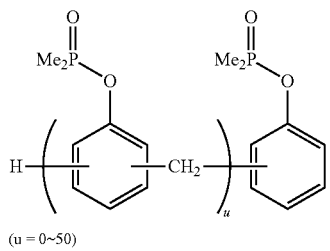
(I-8)

The phosphorus-containing compound of the invention can be prepared by a method shown by the following reaction scheme.

[Chem. 11]

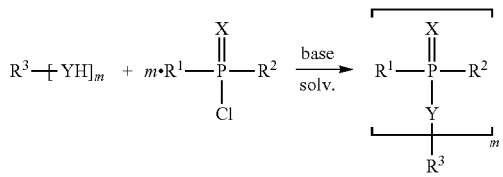

wherein m, $R^1$, $R^2$, $R^3$, X, and Y are same as m, $R^1$, $R^2$, $R^3$, X, and Y defined above.

Examples of the base that can be used in the above reaction include tertiary amines, such as triethylamine, tributylamine, diazabicycloundecene, diazabicyclononene, and 1,4-diazabicyclo[2.2.2]octane; pyridines, such as pyridine and N,N-dimethylaminopyridine; imidazoles, such as 1-methylimidazole; and phosphines, such as triphenylphosphine, tributylphosphine, and tricyclohexylphosphine.

Examples of the solvent that can be used in the above reaction include ketones, such as methyl ethyl ketone, methyl amyl ketone, diethyl ketone, acetone, methyl isopropyl ketone, propylene glycol monomethyl ether acetate, and cyclohexanone; ethers, such as tetrahydrofuran, 1,2-dimethoxyethane, 1,2-diethoxyethane, and propylene glycol monomethyl ether; esters, such as ethyl acetate and n-butyl acetate; aromatic hydrocarbons, such as benzene, toluene, and xylene; halogenated aliphatic hydrocarbons, such as carbon tetrachloride, chloroform, trichloroethylene, and methylene chloride; and halogenated aromatic hydrocarbons, such as chlorobenzene.

The reaction is carried out at a temperature of −80° to 100° C., preferably room temperature to 50° C., for a period of 0.5 to 72 hours, preferably 1 to 24 hours.

The invention also provides a reaction process including causing the above-described phosphorus-containing compound to react with an epoxy compound according to the following reaction scheme.

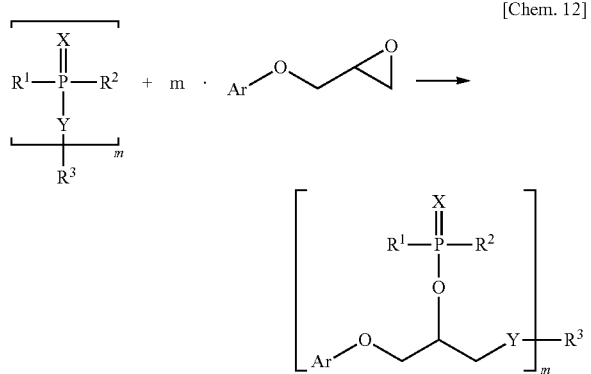

wherein m represents a number of 1 to 10; $R^1$ and $R^2$ each independently represent a hydrogen atom, an alkyl group, or an aryl group; $R^3$ represents an alkyl group, an alkanediyl group, an alkanetriyl group, an alkanetetrayl group, or an aromatic group; X represents an oxygen atom or a sulfur atom; Y represents an oxygen atom, a sulfur atom, or —$NR^4$—; and $R^4$ represents a hydrogen atom, an alkyl group, or an aryl group.

The phosphorus-containing compound of the invention is combined with a polyepoxy compound to provide a curing epoxy resin composition.

Examples of the polyepoxy compound that can be used in the invention include polyglycidyl ether compounds of mononuclear polyhydric phenol compounds, such as hydroquinone, resorcinol, pyrocatechol, and phloroglucinol; polyglycidyl ether compounds of polynuclear polyhydric phenol compounds, such as dihydroxynaphthalene, biphenol, methylenebisphenol (bisphenol F), methylenebis(o-cresol), ethylidene bisphenol, isopropylidene bisphenol (bisphenol A), isopropylidene bis(o-cresol), tetrabromobisphenol A, 1,3-bis(4-hydroxycumylbenzene), 1,4-bis(4-hydroxycumylbenzene), 1,1,3-tris(4-hydroxyphenyl)butane, 1,1,2,2-tetra(4-hydroxyphenyl)ethane, thiobisphenol, sulfonylbisphenol, oxybisphenol, phenol novolak, o-cresol novolak, ethylphenol novolak, butylphenol novolak, octylphenol novolak, resorcin novolak, terpene phenol; polyglycidyl ethers of polyhydric alcohols, such as ethylene glycol, propylene glycol, butylene glycol, hexanediol, polyethylene glycol, thiodiglycol, glycerol, trimethylolpropane, pentaerythritol, sorbitol, and bisphenol A-ethylene oxide adduct; homopolymers or copolymers of glycidyl methacrylate or a glycidyl ester of an aliphatic, aromatic or alicyclic polybasic acid, such as maleic acid, fumaric acid, itaconic acid, succinic acid, glutaric acid, suberic acid, adipic acid, azelaic acid, sebacic acid, dimer acid, trimer acid, phthalic acid, isophthalic acid, terephthalic acid, trimellitic acid, trimesic acid, pyromellitic acid, tetrahydrophthalic acid, hexahydrophthalic acid, or endomethylene tetrahydrophthalic acid; epoxy compounds having a glycidylamino group, such as N, N-diglycidylaniline, bis (4-(N-methyl-N-glycidylamino)phenyl)methane and diglycidyl o-toluidine; epoxidized cyclic olefins, such as vinylcyclohexene diepoxide, dicyclopentanediene diepoxide, 3,4-epoxycyclohexylmethyl-3,4-epoxycyclohexane carboxylate, 3,4-epoxy-6-methylcyclohexylmethyl-6-methylcyclohexane carboxylate, and bis(3,4-epoxy-6-methylcyclohexylmethyl) adipate; epoxidized conjugated diene polymers, such as epoxidized polybutadiene and an epoxidized styrene-butadiene copolymer; and heterocyclic compounds, such as triglycidyl isocyanurate. These epoxy resins may be internally crosslinked by a prepolymer of the terminal isocyanate or may have their molecular weight increased by a polyvalent active hydrogen compound (e.g., polyhydric phenols, polyamines, carbonyl-containing compounds, and polyphosphoric esters).

The polyepoxy compound preferably has an epoxy equivalent of from 70 to 3,000, more preferably 90 to 2,000. With an epoxy equivalent less than 70, the physical properties of the cured product can reduce. With an epoxy equivalent larger than 3,000, curability can be insufficient.

The curing epoxy resin composition of the invention is preferably combined with a curing catalyst, such as p-dimethylaminopyridine, triphenylphosphine, imidazole, tertiary amines, phosphines, quaternary ammonium salts, and quaternary phosphonium salts.

The curing epoxy resin composition of the invention is preferably combined with a general-purpose epoxy resin curing agent. Suitable epoxy resin curing agents include imidazoles, such as 2-ethyl-4-methylimidazole, 1,2-dimethylimidazole, and 1-(2-methylimidazol-1-ylmethyl)naphthalen-2-ol; polyalkylpolyamines, such as diethylenetriamine, triethylenetriamine, and tetraethylenepentamine; alicyclic polyamines, such as 1,2-diaminocyclohexane, 1,4-diamino-3,6-diethylcyclohexane, and isophoronediamine; and aromatic polyamines, such as m-xylylenediamine, diaminodiphenylmethane, and diaminodiphenyl sulfone. Further included are polyepoxy adducts of these polyamines obtained by the reaction with various epoxy resins, such as glycidyl ethers (e.g., phenyl glycidyl ether, butyl glycidyl ether, bisphenol A diglycidyl ether, and bisphenol F glycidyl ether) or carboxylic acid glycidyl esters in a usual manner; amide-modified products of the organic polyamines obtained by the reaction with carboxylic acids (e.g., phthalic acid, isophthalic acid, and dimer acid) in a usual manner; and Mannich-modified products of the polyamines obtained by the reaction with aldehydes (e.g., formaldehyde) and phenols having at least one aldehyde-reactive site on their nucleus (e.g., phenol, cresol, xylenol, tert-butylphenol, and resorcinol) in a usual manner. Furthermore, latent curing agents, such as dicyandiamides, acid anhydrides, and imidazoles, are also useful.

If necessary, the curing epoxy resin composition may contain commonly used additives, including reactive or nonreactive diluents (plasticizers), such as monoglycidyl ethers, dioctyl phthalate, dibutyl phthalate, benzyl alcohol, and coal tar; fillers or pigments, such as glass fiber, carbon fiber, cellulose, silica sand, cement, kaolin, clay, aluminum hydroxide, bentonite, talc, silica, finely divided silica, titanium dioxide, carbon black, graphite, iron oxide, and bituminous materials; silane coupling agents, such as γ-aminopropyltriethoxysilane, N-β-(aminoethyl)-γ-aminopropyltriethoxysilane, N-β-(aminoethyl)-N'-β-(aminoethyl)-γ-aminopropyltriethoxysilane, γ-anilinopropyltriethoxysilane, γ-glycidoxypropyltriethoxysilane, β-(3,4-epoxycyclohexyl)ethyltriethoxysilane, vinyl triethoxysilane, N-β-(N-vinylbenzylaminoethyl)-γ-aminopropyltriethoxysilane, γ-methacryloxypropyltrimethoxysilane, γ-chloropropyltrimethoxy silane, and γ-mercaptopropyltrimethoxysilane; lubricants, such as candelilla wax, carnauba wax, Japan wax, insect wax, beeswax, lanolin, spermaceti wax, montan wax, petroleum wax, aliphatic acid wax, aliphatic esters, aliphatic ethers, aromatic esters, and aromatic ethers; thickeners; thixotropic agents; antioxidants; light stabilizers; UV absorbers; flame retardants; defoamers; rust inhibitors; colloidal silica, and colloidal alumina. Adhesive resins, such as xylene resin and petroleum resins, may be used in combination.

The curing epoxy resin composition of the invention can be used for a wide range of applications, such as coatings or adhesives for concrete, cement mortar, various metals, leather, glass, rubber, plastics, wood, cloth, and paper; pressure-sensitive adhesives for packaging adhesive tape, adhesive labels, labels for frozen foods, removable labels, labels for POS system, adhesive wallpaper, and adhesive flooring; processed paper, such as art paper, light-weight coated paper, cast-coated paper, coated paperboard, carbonless copy paper, and impregnated paper; textile processing agents, such as sizing agents, anti-fray agents, and processing agents for natural fibers, synthetic fibers, glass fiber, carbon fiber, and metal fibers; building materials, such as sealants, cement admixtures, and waterproof materials; and sealants for electronic/electric devices.

EXAMPLES

The invention will now be illustrated in greater detail, but it should be understood that the invention is not deemed to be limited thereto.

Example 1

Synthesis of Phosphorus-containing Compound [I-1]

A 100 ml three-necked flask equipped with a rotor, a reflux tube, and a rubber septum was thoroughly dried, purged with nitrogen, and charged with 0.75 g (8.8 mmol) of phenol, 0.89 g (8.8 mmol) of triethylamine, and 3 ml of ultra-dehydrated tetrahydrofuran using a syringe. In another vessel were put 0.90 g (8 mmol) of dimethyl phosphinic chloride and 3 ml of ultra-dehydrated tetrahydrofuran to prepare a dimethyl phosphinic chloride solution. The dimethyl phosphinic chloride solution was added dropwise using a syringe taking care so that the reaction temperature did not exceed 30° C. After completion of the addition, the reaction system was stirred overnight. To the reaction solution were added 5 ml of a saturated ammonium chloride aqueous solution and 5 ml of water, followed by stirring well. The solution was transferred to a separatory funnel, extracted 3 times with 10 ml portions of ethyl acetate to obtain an organic layer. The organic layer was washed with 10 ml of water and dried over anhydrous magnesium sulfate. The solvent was removed using an evaporator to give pale yellow liquid (crude yield: 60.3%, GC purity: 87.1%). The crude product was purified by column chromatography (stationary phase: silica gel, mobile phase: ethyl acetate, Rf=0.07) to give the desired phosphorus-containing compound [I-1] as white crystals (overall yield: 45.8%, GC purity: >99%, $^{31}$P-NMR: 52.44 ppm). The $^{1}$H-NMR, $^{31}$P-NMR, and GC-MS spectra of the resulting phosphorus-containing compound are shown in FIGS. 1 to 3, respectively.

Example 2

The phosphorus-containing compound [I-1] weighing 17.0 mg (0.25 mmol) and 20.6 mg (0.25 mmol) of Adeka Glycirol ED-509S were allowed to react with each other in the presence of 0.9 mg (7.5 mol %) of DMAP as a catalyst in a nitrogen stream at 160° C. for 2 hours. P2 shown in [Chem. 13] described below was obtained with high selectivity according to the reaction mechanism shown in [Chem. 13] described below. The $^{1}$H-NMR, $^{31}$P-NMR, and GC-MS spectra of the resulting P2 are shown in FIGS. 4 to 6, respectively.

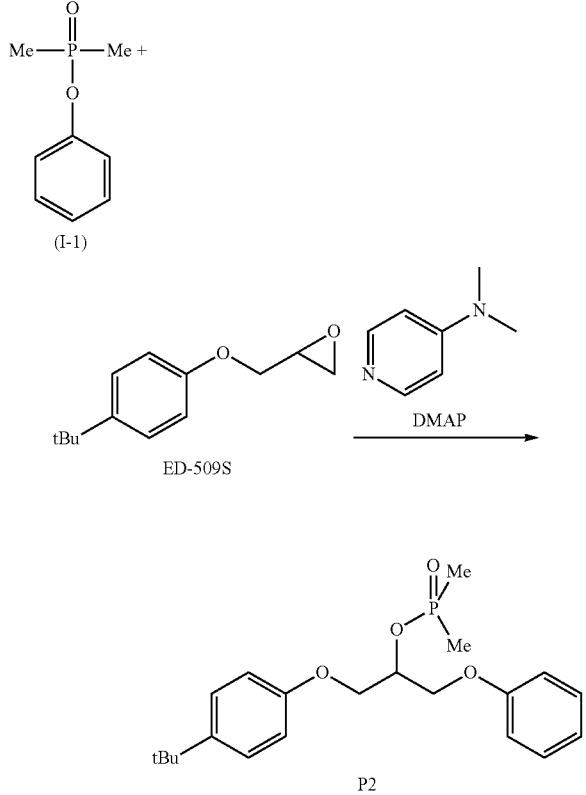

[Chem. 13]

Example of the invention proved that the phosphorus-containing compound of the invention has reactivity with a glycidyl group. Incorporation of the phosphorus-containing compound of the invention into an epoxy resin provides an epoxy resin cured product that is expected to have flame retardancy and a reduced dielectric constant without causing reduction in physical properties of the cured product.

The invention claimed is:

1. A phosphorus-containing compound represented by following formula (I):

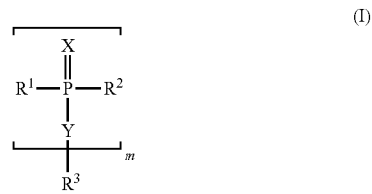

wherein:

m represents an integer from 1 to 4;

$R^1$ and $R^2$ each independently represent an alkyl group;

$R^3$ represents an aromatic group represented by a formula selected from the group consisting of:

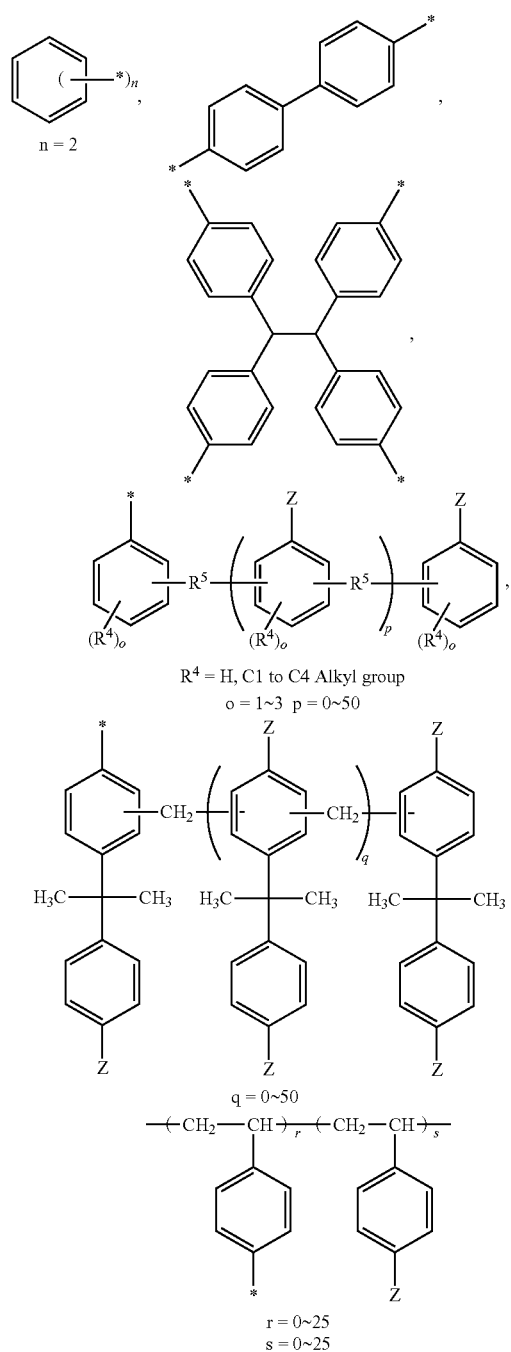

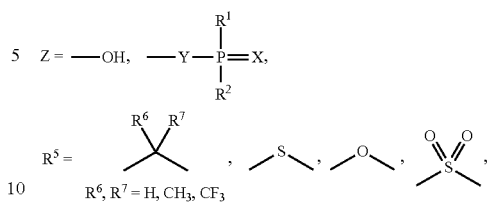

wherein:

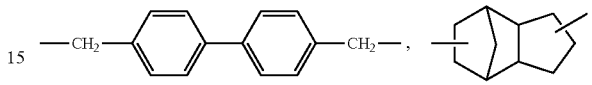

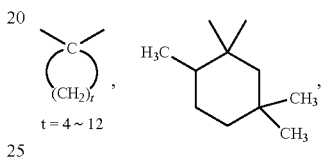

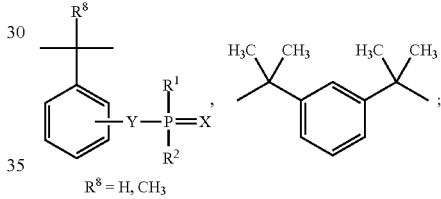

\* represents a bonding hand; X represents an oxygen atom;
and Y represents an oxygen atom.

2. The phosphorus-containing compound according to claim 1, wherein $R^1$ is an alkyl group having 1 to 5 carbon atoms, and $R^2$ is an alkyl group having 1 to 5 carbon atoms.

3. A curing epoxy resin composition comprising the phosphorus-containing compound according to claim 1, and a polyepoxy compound.

4. A curing epoxy resin composition comprising the phosphorus-containing compound according to claim 2, and a polyepoxy compound.

\* \* \* \* \*